(12) United States Patent
Self

(10) Patent No.: US 11,723,878 B2
(45) Date of Patent: Aug. 15, 2023

(54) METHODS FOR PRODUCING FULLERENE THAT IS BIOAVAILABLE VIA INHALATION OR OTHER ABSORPTION MODALITY

(71) Applicant: Aaron Self, Louisville, KY (US)

(72) Inventor: Aaron Self, Louisville, KY (US)

( * ) Notice: Subject to any disclaimer, the term of this patent is extended or adjusted under 35 U.S.C. 154(b) by 255 days.

(21) Appl. No.: 17/129,697

(22) Filed: Dec. 21, 2020

(65) Prior Publication Data
US 2022/0193239 A1 Jun. 23, 2022

(51) Int. Cl.
| | |
|---|---|
| *A61K 9/70* | (2006.01) |
| *D21H 27/00* | (2006.01) |
| *C01B 32/156* | (2017.01) |
| *A61M 15/06* | (2006.01) |
| *A61K 33/44* | (2006.01) |
| *A24D 1/02* | (2006.01) |
| *D21H 19/38* | (2006.01) |
| *A61K 33/243* | (2019.01) |
| *A61K 31/20* | (2006.01) |

(52) U.S. Cl.
CPC .............. *A61K 9/7007* (2013.01); *A24D 1/02* (2013.01); *A61K 33/44* (2013.01); *A61M 15/06* (2013.01); *C01B 32/156* (2017.08); *D21H 19/38* (2013.01); *D21H 27/00* (2013.01); *A61K 31/20* (2013.01)

(58) Field of Classification Search
CPC ...... A61K 9/7007; A61K 33/44; A61K 31/20; A24D 1/02; A61M 15/06; C01B 32/156; D21H 19/38; D21H 27/00
See application file for complete search history.

(56) References Cited

U.S. PATENT DOCUMENTS 10,342,797 B2 * 7/2019 Mitchell ................ A61K 47/02

OTHER PUBLICATIONS

Oya et al. https://www.techconnectworld.com/World2018/wednesday.html#W6.313 (Year: 2018).*
Miglyol® 812 Technical data sheet, Jul. 2016, [retrieved Mar. 3, 2023], from the Internet <URL:https://tr.organic-materials.com/cms/wp-content/uploads/2020/09/MIGLYOL_812_TDSC-3.pdf (Year: 2016).*
Semenov, K. N., et al. Russian Journal of Applied Chemistry 80 (2007): 557-561 (Year: 2007).*
Laugesen et al. Tobacco Control 2003;12:406-410. (Year: 2003).*

* cited by examiner

*Primary Examiner* — Mina Haghighatian
*Assistant Examiner* — Janice Y Silverman
(74) *Attorney, Agent, or Firm* — Cummins Intellectual Property (IP) Law PLLC

(57) ABSTRACT

Implementations set forth herein relate to systems, methods, and apparatuses associated with fullerene-containing materials. In some implementations, a fullerene-containing material is disposed over a substrate of a smoke-able product in order to inhibit an allergic response (e.g., coughing) from a user who smokes or otherwise ingests the smoke-able product. Various fullerene-containing materials can be generated using a carbon substance that undergoes one or more process operations in order for fullerene molecules to be available for inclusion in the various materials. In some implementations, one or more other fullerene-containing materials can be generated through an at least partially organic process of feeding a particular plant a fullerene-containing plant food.

6 Claims, 7 Drawing Sheets

METHODS FOR PRODUCING FULLERENE THAT IS BIOAVAILABLE VIA INHALATION OR OTHER ABSORPTION MODALITY

BACKGROUND

Concentrations of substances that inhibit allergic responses can be applied to individual cells in a laboratory dish in order to observe responses of those individual cells. However, making such substances bioavailable so that those same benefits can be exhibited in humans may necessitate further alteration to the substances. This can, in part, be due to allergic responses that can result when a person ingests a substance to achieve certain benefits. In some instances, this can result in a wasting of resources that may have been consumed when developing a drug or other substance for use in humans. Although certain materials can be available for consuming with a drug or other substance in order to improve the chances of making the drug or other substance bioavailable, there may be negative consequences to ingesting such combinations. For example, certain combinations of materials and drugs can degrade the quality and/or benefits of a drug. Consequently, additional resources and energy may be consumed in attempts to further mitigate any adverse effects.

SUMMARY

Implementations set forth herein relate to systems, methods, apparatuses, and materials for providing a bioavailable form of fullerene that can be absorbed into the human body via inhalation and/or other modality for ingesting a substance. Alternatively, or additionally, the bioavailable form of fullerene can be absorbed into one or more different plants and/or one or more different materials. In some implementations, fullerene particles can be disposed onto a flexible substrate, which can be used to retain one or more smoke-able products. For instance, the flexible substrate can include, but is not limited to, paper, wax, gel, and/or any other material which can be used by a person to at least partially retain a substance for purposes of smoking. When the fullerene is disposed onto the flexible substrate and the flexible substrate is heated, a vapor emitted from the flexible substrate and the substance (e.g., a plant) can be inhaled by the person. As a result of the inhalation, the person can receive molecules of fullerene from the flexible substrate, as well as other plant molecules. Incorporating the fullerene into the inhaled vapor allows certain health benefits to be experienced by the person. For example, the fullerene that is inhaled can mitigate and/or prevent an allergic reaction (e.g., coughing) that persons may otherwise experience when smoking certain plants. This can improve absorption of beneficial substances while mitigating adverse effects from smoking.

In some implementations, molecules of fullerene that are incorporated into a material for smoking can have a variety of different properties. For example, multiple different fullerene molecules that are disposed onto a material for ingestion can have varying diameters. For instance, the fullerene molecules that are applied to a material can include a first fullerene molecule having a first diameter and a second fullerene molecule that is a second diameter, which is greater than the first diameter. In this way, physiological benefits of each respective size of fullerene molecule can be realized for a user who ingests the material. Alternatively, the fullerene molecules that are included in a particular material can have the same diameter and/or the same number of carbon atoms, thereby limiting adverse physiological effects that some persons may experience when ingesting fullerene molecules of a certain size. In some implementations, the fullerene molecules that are incorporated into a material can have a range of diameters. For example, the diameters of fullerene molecules incorporated into a material (e.g., plant or non-plant) can be less than 1000 nanometers.

In some implementations, a fluid that includes fullerene can be generated using one or more different operations. The resulting fluid can have a fullerene concentration that is greater than or equal to 0.1 gram per liter, 0.1 grams per liter, 0.25 grams per liter, 0.28 grams per liter, 0.3 grams per liter, and/or 0.35 grams per liter. The fluid, and/or a derivative of the fluid, can then be disposed over a surface of a smoke-able material, incorporated into an ingestible fluid, and/or provided as food for a plant. In order to generate the fluid, a carbon-containing substance and a liquid can be combined as a mixture, which can be filtered in order to remove certain carbon-containing particles of a certain size and/or remove certain particles of the liquid that have a certain size or feature. For example, a fritted glass filter can be used to filter out certain liquid particles and/or certain carbon particles. The resulting filtered fluid can be fed to plants in order that the plants will absorb some amount of the fullerene molecules as the plants grow.

In some implementations, the filtered fluid can be placed into a container and at least a portion of the liquid can be removed in order to leave fullerene particles on one or more surfaces of the container. Initially, the fullerene particles may already be present in the carbon-containing substance but may not be readily accessible without undertaking the aforementioned operations. In some implementations, the carbon-containing substance can be mixed into a liquid (e.g., distilled water, toluene, MCT oil, and/or any other substance), filtered, and the liquid can be at least partially removed from the container using evaporation. When the fullerene is dissolved into the liquid and, subsequently, the liquid is evaporated, the fullerene can remain on one or more surfaces of the container as a film. In some implementations, the fullerene remaining on and/or in the container can be incorporated into a mixture by introducing another liquid into the container and/or otherwise removing the remaining fullerene from the container and introducing the removed fullerene into another liquid.

For example, the remaining fullerene can be removed from the one or more surfaces of the container and dissolved into a liquid such as, but not limited to, distilled water, deionized water, toluene, capric acid, caprylic acid, and/or any other substance or combinations of substances in which fullerene can be mixed. In some implementations, distilled water is introduced into the container and an ultransonic mixer and/or ultrasonic transducer is used to dissolve the remaining fullerene into the distilled water. The mixing can occur, in the container or a different container, over a period of time until the concentration of fullerene molecules in the distilled water reaches an amount that is greater than or equal to 0.1 gram per liter, 0.2 grams per liter, 0.25 grams per liter, 0.28 grams per liter, 0.3 grams per liter, 0.35 grams per liter, and/or any other suitable concentration. In some implementations, the fullerene that is removed from the container can include molecules of the same or different diameters of fullerene.

In some implementations, a fullerene solution can be incorporated onto and/or into a flexible substrate that can be used to hold a smoke-able product (i.e., a product that is capable of being smoked by a person). The fullerene solution can be applied to the flexible substrate such that one or more layers of the flexible substrate abut at least one or more fullerene molecules. When the fullerene solution is applied to the flexible substrate, heating of the flexible substrate and smoke-able product can yield a vapor that (i) includes the fullerene molecules, and (ii) can be inhaled by a user in order for the user to realize physiological benefits of the fullerene. Although certain wave lengths of light may be harmful to particular molecules of fullerene—nonetheless, the vaporization of the flexible substrate with the fullerene molecules allows for a user to receive the benefits of the fullerene (e.g., mitigation of allergic reaction from smoking, reduce oxidative stress, etc.).

In some implementations, fullerene molecules that are extracted according to one or more processes discussed herein can be incorporated into a carrier solvent and/or extraction solvent. These solvents can include, but are not limited to, acetone, benzyl alcohol, 1,3-butylene glycol, carbon dioxide, castor oil, citric acid esters of mono- and di-glycerides, ethyl acetate, ethyl alcohol (ethanol), glycerol (glycerin), glyceryl diacetate, glyceryl triacetate (triacetin), glyceryl tributyrate (tributyrin), hexane, isopropyl alcohol (isopropanol), methyl alcohol (methanol), methyl ethyl ketone (2-butanone), methylene chloride (dichloro-methane), monoglycerides and diglycerides, monoglyceride citrate, 2-nitropropane, 1,2-propylene glycol (1,2-propanediol), propylene glycol mono-esters and diesters of fat-forming fatty acids, triethyl citrate, and/or any combination thereof. The combination of the fullerene molecules and solvent(s) can be incorporated into one or more products such as, but not limited to, smoke-able substrates, smoke-able fluids, ingestible solids, ingestible liquids, ingestible gases, and/or any other product that can be ingested by a living species.

In some implementations, fullerene molecules that are extracted according to one or more processes discussed herein can be derived from graphite, ash, carbon glass, coal, crystal, and/or any other source of carbon. When the fullerene molecules are extracted, they can be mixed into a substance, such as, but not limited to, MCT oil, lubricant, and/or mineral oil. For example, the fullerene molecules can be mixed into capric acid and/or caprylic acid. When the fullerene molecules are initially mixed into the capric acid and caprylic acid, the mixture can initially exhibit one or more characteristics, but these one or more characteristics can change as the mixture is further processed. For example, initially the mixture can exhibit a first degree of opacity and/or a first degree of reflectance, but as the mixture is further agitated and/or mixed, the mixture can exhibit a second degree of opacity and/or a second degree of reflectance. In some implementations, the mixture can be agitated until one or more characteristics are exhibited by the mixture in order to ensure that the fullerene molecules are suitably arranged into the capric acid and caprylic acid. For example, the mixture can be agitated until the mixture exhibits a change in opacity (e.g., becomes more or less transparent) and/or exhibits a change in reflectance (e.g., more or less light reflects from the mixture). In some implementations, the mixture can be filtered before and/or subsequent to the changes in opacity and/or reflectance, in order to further remove particles of a certain size and/or shape from the mixture. For example, the mixture of capric acid, caprylic acid, and fullerene molecules can be filtered (e.g., using a fritted glass filter) until the mixture becomes more transparent and/or in order to remove carbon particles of a certain size (e.g., greater than 1000 nm in length and/or diameter).

The above description is provided as an overview of some implementations of the present disclosure. Further description of those implementations, and other implementations, are described in more detail below.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1:
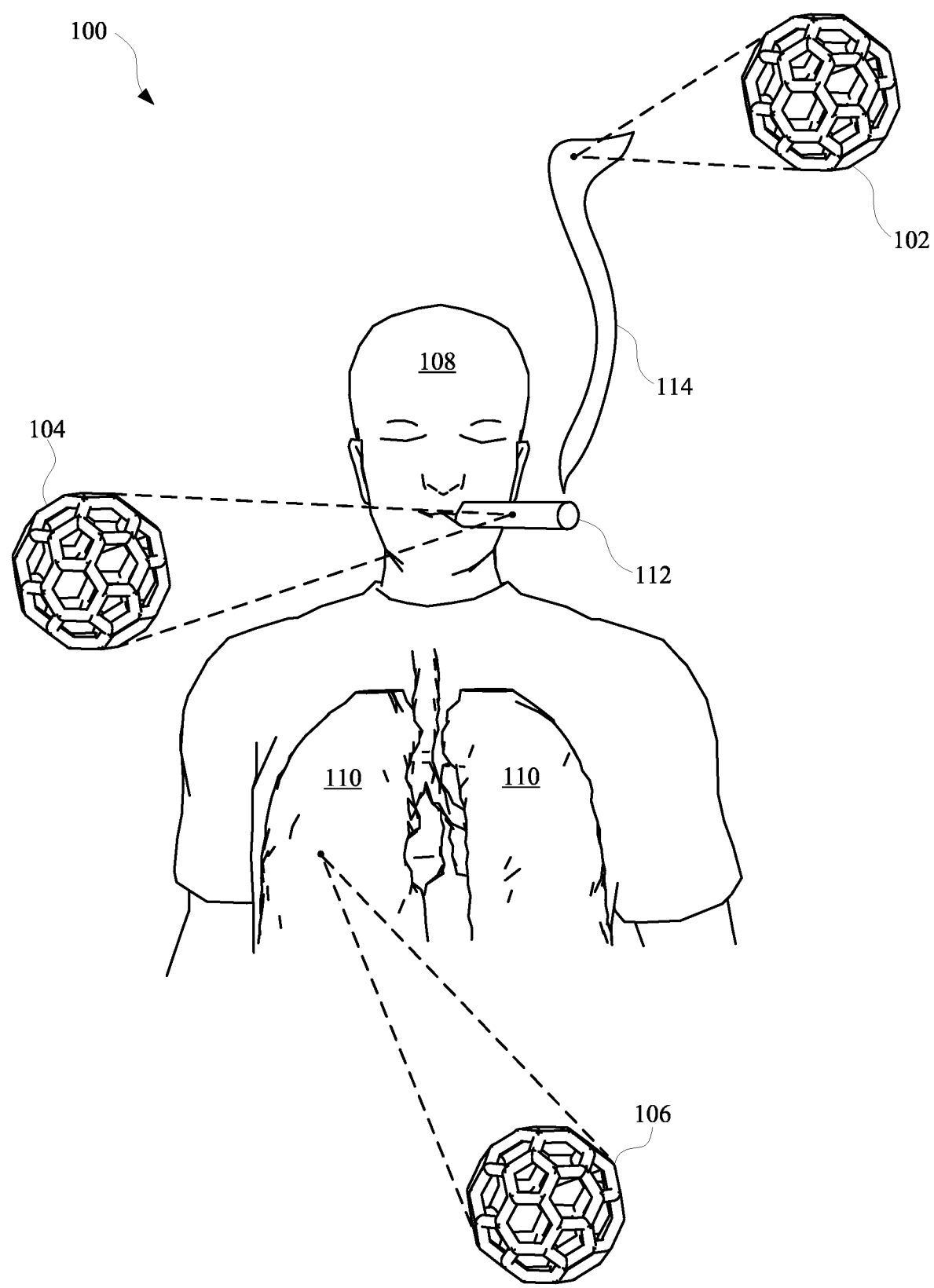
FIG. 1 illustrates a view of a user ingesting fullerene molecules via inhalation of a material that can retain a smoke-able product.

FIG. 1 illustrates a view 100 of a user 108 ingesting fullerene molecules via inhalation of a material that retains a smoke-able product. The fullerene molecules (102, 104, 106) can initially be incorporated with material 112 that can be used to retain a smoke-able product. For example, the smoke-able product can be a plant or other material that can be at least partially enveloped by the material 112. When the material 112 is heated, a vapor 114 can be available for inhalation by the user 108. The vapor 114 can contain fullerene molecules 102, due to the presence of fullerene molecules 104 on the material 112. When the user 108 inhales the vapor 114, the lungs 110 of the user 108 can receive fullerene molecules 106, which can provide health benefits to the user 108.

In some implementations, the fullerene molecules (102, 104, 106) can be embodied in a mixture that is disposed over one or more surfaces of the material 112 and/or absorbed into one or more layers of the material 112. For example, the material 112 can be a fibrous and/or flexible substrate that has one or more layers, and the fullerene molecules (102, 104, 106) can mixed into a solution that is disposed over the fibrous and/or flexible substrate. In some implementations, the solution can include distilled water, toluene, capric acid, caprylic acid, oil, wax, and/or any combination of materials that can be disposed onto a smoke-able material. Although certain types of vapors, such as smoke from a fibrous material, can invoke an allergic reaction (e.g., coughing) from various persons, the ingestion of the fullerene molecules 106 can inhibit the allergic reaction. In this way, certain smoke-able products that have health benefits can be more readily tolerated when the material 112 containing the fullerene molecules 104 is used when ingesting the smoke-able products via inhalation. Furthermore, the material 112 can allow for better absorption of the smoke-able product by the user 108 because the user 108 would cough less when inhaling the smoke-able product. This can reduce an amount of time and/or energy that would be necessary to produce a suitable dose of the smoke-able product, because less of the smoke-able product would need to be available for the user 108 to ingest when there is no risk of the user 108 coughing out some of the smoke-able product.

Figure 2A:
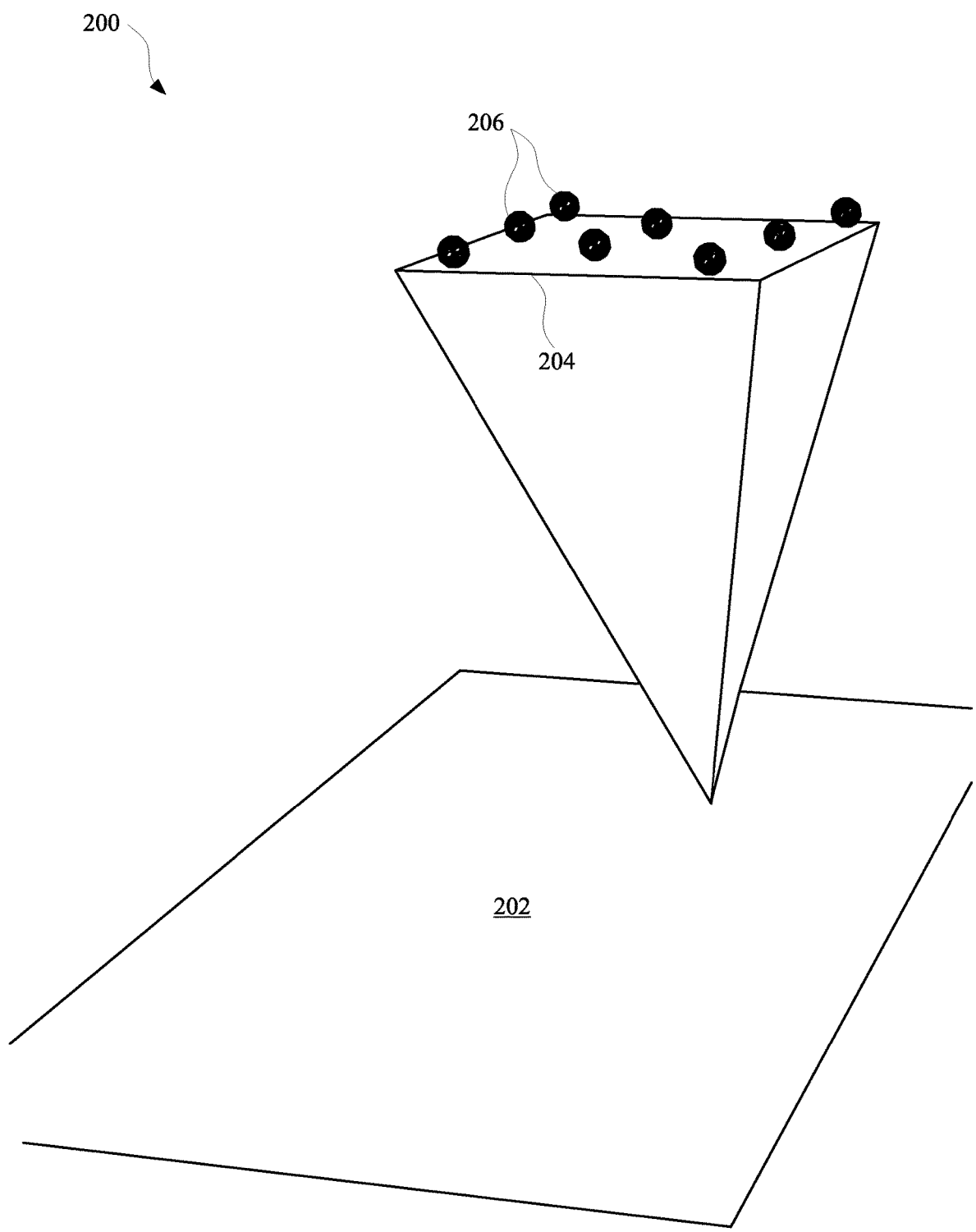
FIG. 2A illustrates a view of a substrate that includes fullerene molecules disposed over one or more surfaces of the substrate.

FIG. 2A illustrates a view 200 of a substrate 202 that includes one or more fullerene molecules 206 disposed over at least a portion of the substrate. The substrate can be a flexible material or a rigid material that can be used to receive a smoke-able product and/or can be combined with a smoke-able product. The view 200 is provided to illustrate the concentration of fullerene molecules 206 that may be disposed over one or more surfaces of the substrate. For example, a portion 204 of the substrate 202 is expanded to provide an estimate of the scale of the fullerene molecules, as well as an optional spacing for the fullerene molecules. This spacing can allow for the fullerene molecules 206 to have some amount of space between each other—at least for some portions of the substrate. For example, a solution of fullerene molecules can be disposed over the substrate 202 in a way that causes a space between fullerene molecules 206 to be greater than a diameter of one or more of the fullerene molecules 206. In some implementations, depending on the composition of the substrate, the fullerene molecules 206 can abut an outer most surface of the substrate. However, in other implementations, the fullerene molecules 206 can be disposed onto an outer most surface and at least partially penetrate the outer most surface.

Figure 2B:
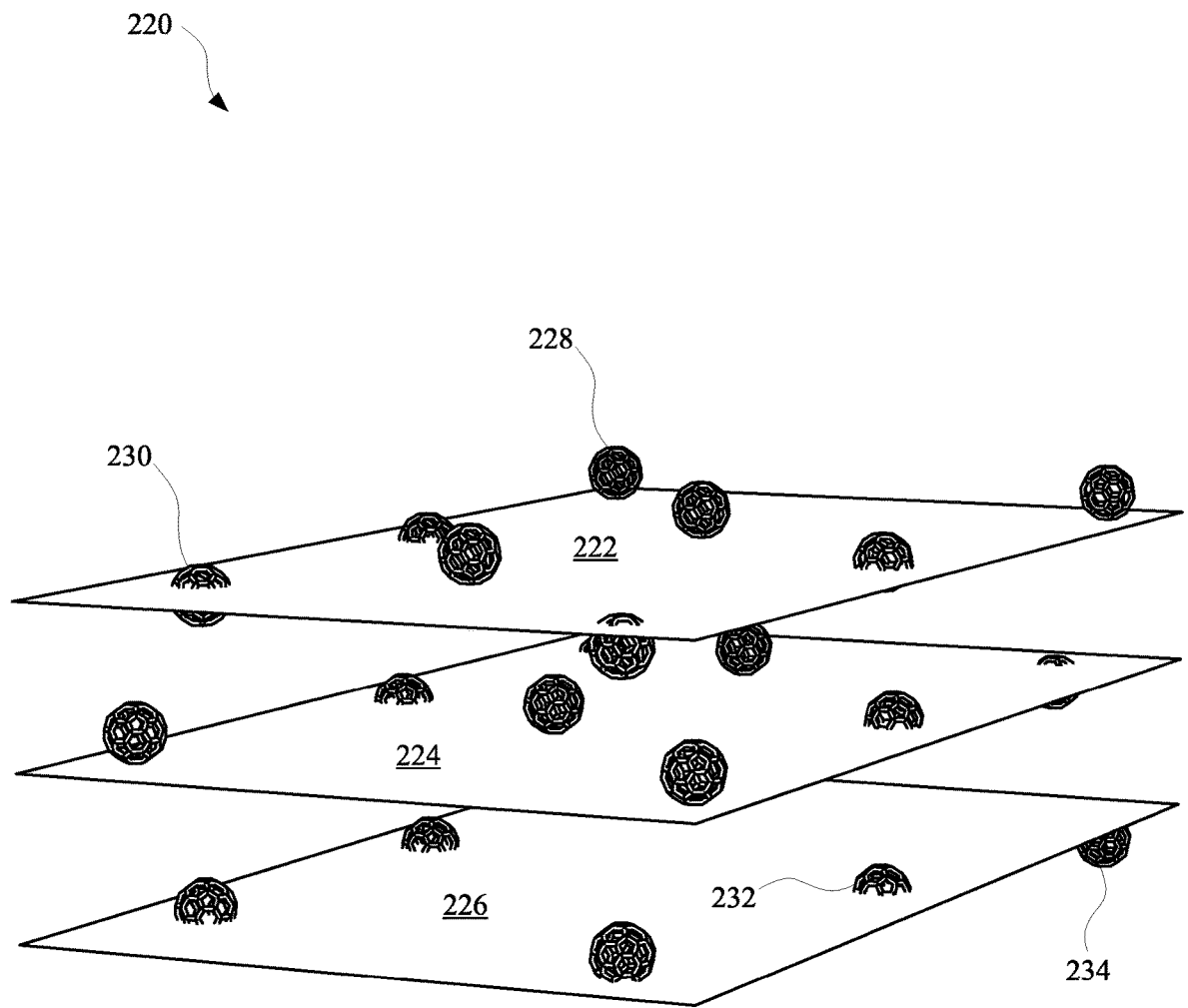
FIG. 2B illustrates a view of a substrate that includes fullerene molecules disposed over and/or within multiple different layers of the substrate.

In some implementations, and as provided in view 220 of FIG. 2B, fullerene molecules (228, 240, 232, 234) can be disposed over multiple surfaces (222, 224, 226) and/or layers of a material. When the surfaces are comprised of a fibrous material, at least some of the fullerene molecules (230, 232) can at least partially penetrate one or more layers of the fibrous material. For example, and as depicted in FIG. 2B, a fullerene molecule 228 can abut an outer most surface of a surface 222, and another fullerene molecule 230 can at least partially penetrate the surface 222. In some implementations, when the material in FIG. 2B has multiple layers, two or more of the layers can be separated by a distance that is greater than a diameter of the fullerene molecules (228, 240, 232, 234). Alternatively, or additionally, when the material in FIG. 2B has multiple layers, two layers can sandwich and/or otherwise contain the fullerene molecules between the two layers so that the outer surfaces of the two layers are not contacting the fullerene molecules. In some implementations, these arrangements can allow for the fullerene molecules to be readily released from a material when a user is smoking the material rather than the fullerene molecules being destroyed by a heat source or light source.

In some implementations, the fibrous material can absorb the fullerene molecules 206 such that the fullerene molecules 206 and the fibrous material can be combined as a homogenous mixture. Alternatively, or additionally, the fullerene molecules 206 can be evenly dispersed throughout all layers of fibrous material that embodies the multiple surfaces (222, 224, 226). In some implementations, a smoke-able product can be soaked with a mixture that includes the fullerene molecules 206 and thereafter cured in order to cause a bond between particles of the smoke-able product and the fullerene molecules 206. The smoke-able product can then be arranged in bulk, in a packaging with other smoke-able products.

Figure 3A:
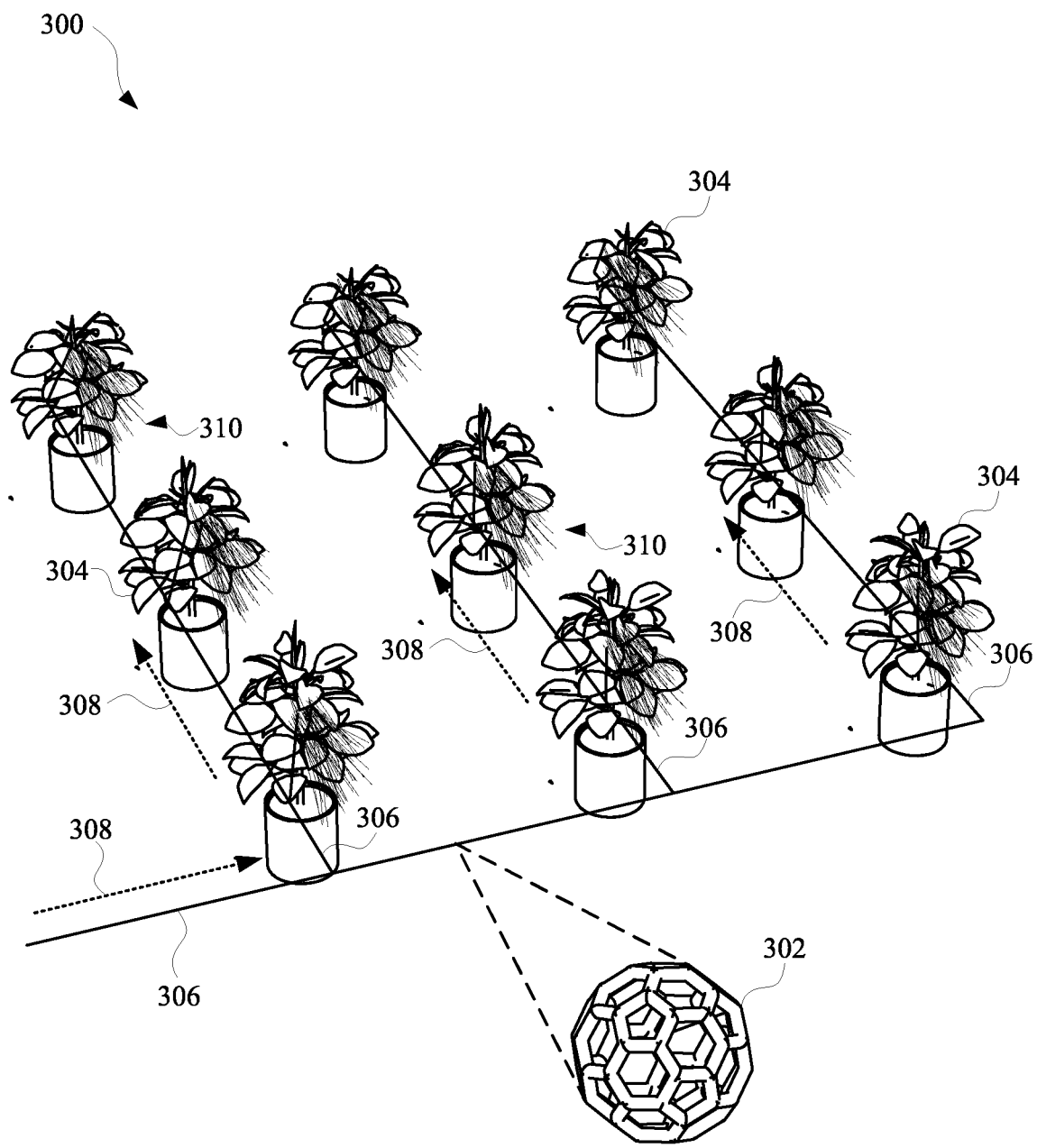
FIG. 3A illustrates a view of one or more different plants being supplied a mixture that includes fullerene molecules when the one or more different plants are at a particular phase(s) in growth.

FIG. 3A illustrates a view 300 of one or more different plants 304 being provided a mixture that includes fullerene molecules 302, in order that the plants 304 can absorb the fullerene molecules 302 as the plants 304 grow. Thereafter, the fullerene molecules 302 can be embodied in one or more portions of the plants 304 and can be used for medical, industrial, and/or other purposes. In some implementations, the mixture that is fed to the plants 304 can include nitrogen and the fullerene molecules 302. For example, the mixture can include nitrate and/or nitrite, and/or any other substance that can be received by a plant and/or a seed via spray 310 or other modality for feeding plants and/or seeds. In some implementations, the nitrate and/or nitrite can be mixed into a solution that also includes fullerene molecules 302, and the solution can be dispensed to the plants 306 via an irrigation system that moves plant food through pipes 306 in a direction 308 of the plants 304.

Figure 3B:
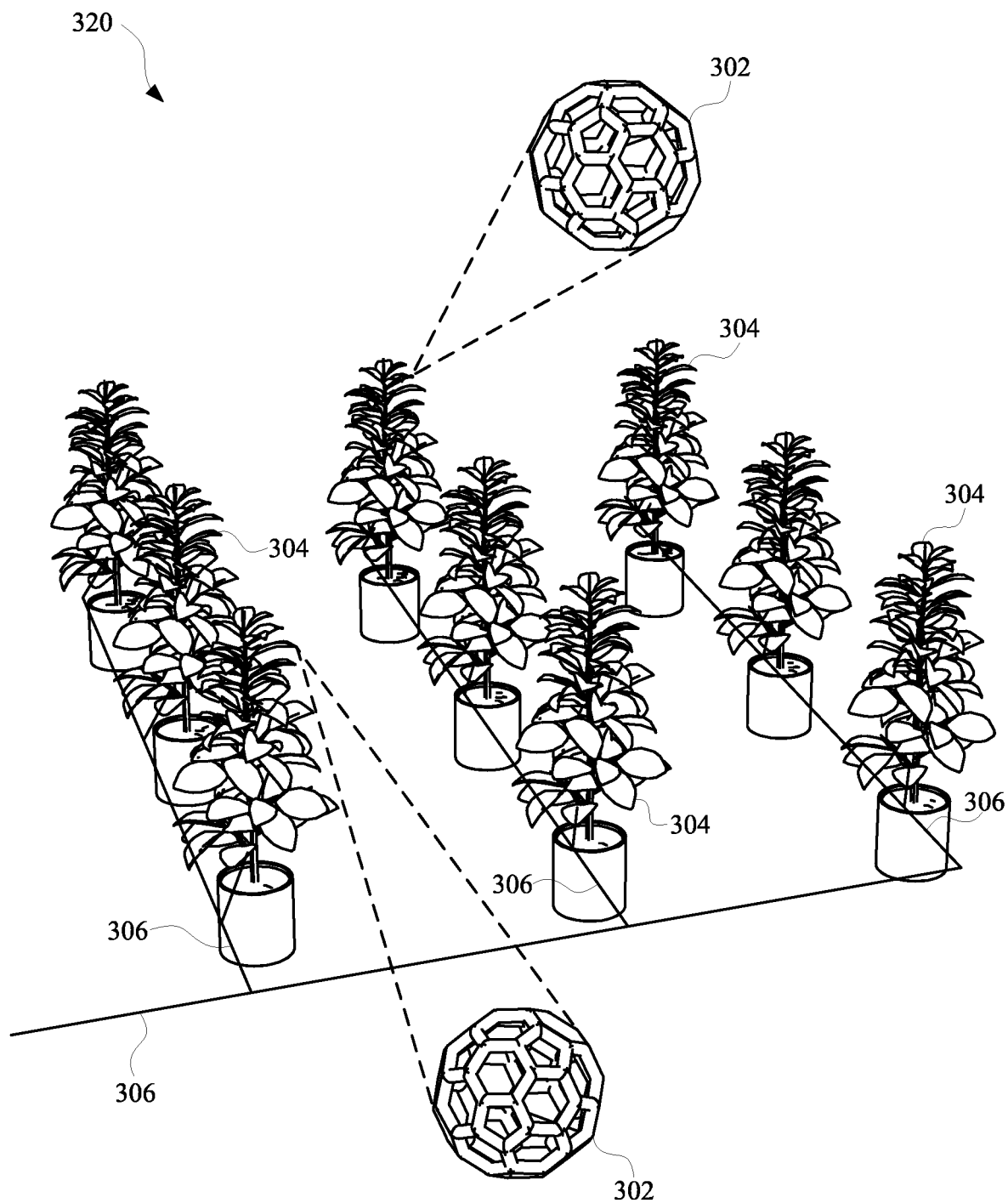
FIG. 3B illustrates a view of plants having fullerene molecules embodied in one or more different portions of the plants while the plants are in a living state.

In some implementations, the mixture can be provided via an irrigation system to seeds and/or plants at one or more different phases of growth. For example, when the plants 304 are entering, or have entered, a flowering phase and/or a budding phase, the mixture can be provided to the plants 304 in order to ensure that the plants 304 absorb the fullerene molecules 302. In other implementations, the before the plants 304 enter a flowering phase and/or a budding phase, the mixture can be introduced to each plant 304 in order that one or more portions of the plants 304 will retain the fullerene molecules as the plants 304 grow. When the plants have absorbed the mixture, and/or otherwise received the mixture, the plants 304 can include fullerene molecules 302 in certain portions of the plants 304, as indicated in view 320 of FIG. 3B.

In some implementations, one or more electroculture techniques can be used to promote absorption of the fullerene molecules by the plants 304. For example, a field can be generated using a direct current (DC) voltage or an alternating current (AC) voltage, or combination thereof, and the field can be provided at a location relative to one or more plants 304 in order to promote movement of the fullerene molecules toward or away from the location. For instance, an electromagnet or a permanent magnet can be arranged above one or more plants 304 in order to encourage movement of the fullerene molecules from a lower portion (e.g., roots, base, stem, etc.) of the one or more plants 304 to a higher portion of the one or more plants 304 (e.g., a portion that includes flowers, leaves, buds, etc.). In this way, when a higher concentration of fullerene molecules is desired for a particular portion of a plant 304, the electroculture can be employed to promote higher concentrations of fullerene molecules in certain portions of the plant 304.

Figure 4:
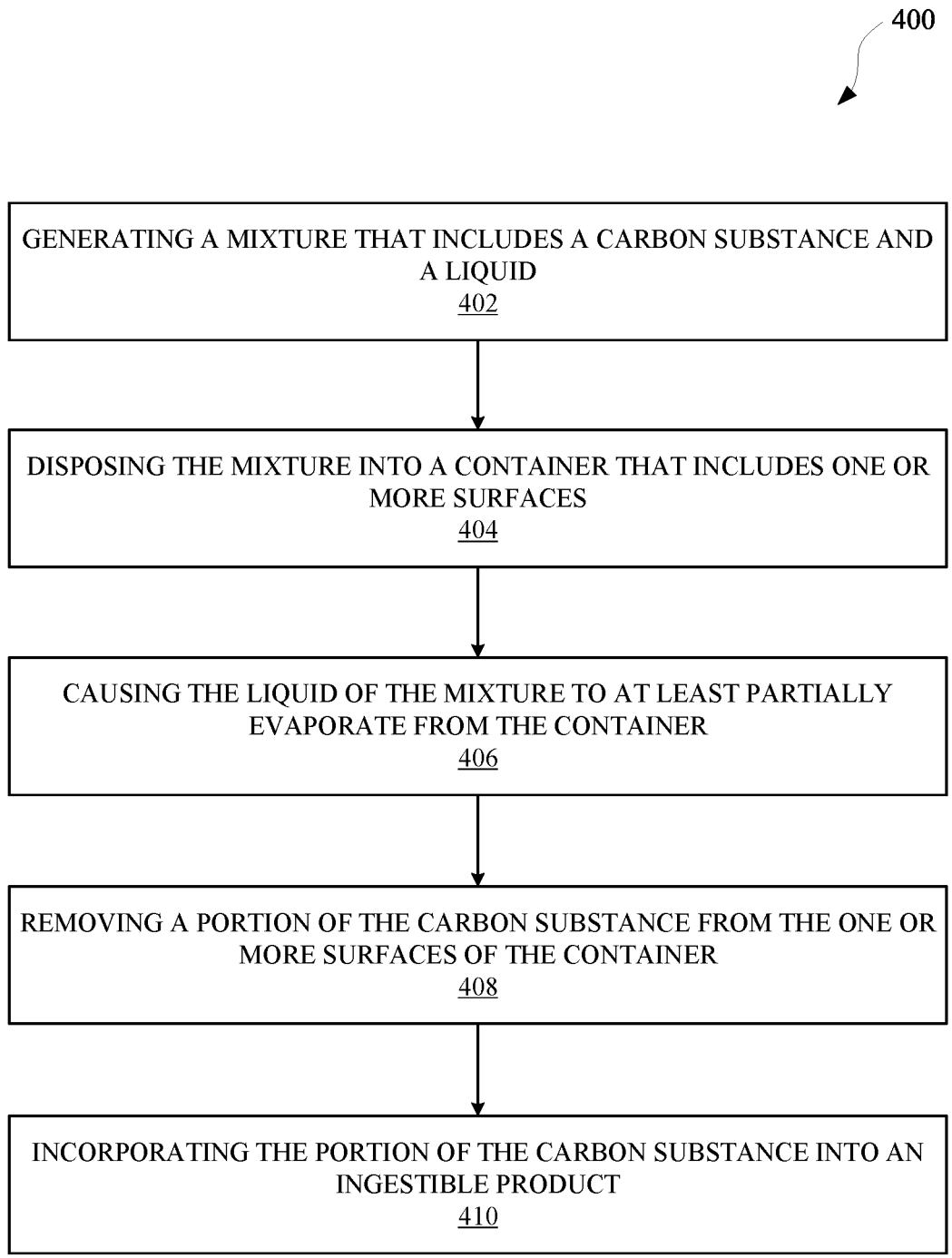
FIG. 4 illustrates a method for producing an ingestible product that includes fullerene molecules.

FIG. 4 illustrates a method 400 for creating an ingestible product that includes fullerene molecules. The method 400 can be performed by employing one or more persons, organisms, chemicals, devices, applications, and/or any suitable combination thereof. The method 400 can include an operation 402 of generating a mixture that includes a carbon substance and a liquid. The carbon substance can include fullerene molecules and/or other forms of carbon, which can be used to derive fullerene molecules. In some implementations, the carbon substance can be an ash that can form on a surface as a result of one or more processes such as, but not limited to, burning, combustion, arcing, electrolysis, compression, and/or any other suitable process for providing a carbon substance. For example, the carbon substance can be generated by causing an amount of voltage to arc between two or more graphite electrodes, and a resulting substance on the surface of the electrodes can contain fullerene molecules.

The method 400 can proceed from operation 402 to an operation 404, which can include disposing the mixture into a container that includes one or more surfaces. In some implementations, the mixture can be put into a glass container with one or more surfaces and/or any other type of container that can be formed from any suitable material. The method 400 can proceed from operation 404 to an operation 406, which can include causing the liquid of the mixture to at least partially evaporate from the container. In some implementations, the liquid can be evaporated using an ultrasonic evaporator and/or transducer, which can cause the liquid to transition to a vapor as a result of vibrations. Alternatively, or additionally, the liquid can be evaporated using some amount of heat and/or other energy in order to cause the liquid to leave the container while leaving behind the carbon substance, which can include fullerene molecules.

The method 400 can proceed from operation 406 to an operation 408, which can include removing a portion of the carbon substance from the one or more surfaces of the container. In some implementations, removal of a portion of the carbon substance can be performed using another liquid that is disposed into the container and mixed until the portion of the carbon substance is dissolved into the liquid. For example, a stirring apparatus can be used to stir the other liquid in the container in order to cause the carbon substance to be displaced from one or more surfaces of the container. The method 400 can proceed from operation 408 to an operation 410, which can include incorporating the portion of the carbon substance, which can include fullerene molecules, into an ingestible product. In some implementations, the ingestible product can be a smoke-able product such as fluid and/or wax for vaporizing, a paper or other substrate for smoking, a plant that can be smoked, and/or any other smoke-able product. In some implementations, the ingestible product can be a carrier solvent that can be ingested by a living organism and/or incorporated into an industrial product.

In some implementations, fullerene molecules may have an atomic structure and/or arrangement that can be compromised by certain frequencies of light. This may indicate to some of ordinary skill in related art that fullerene molecules are not suitable for incorporation into a smoke-able product—at least if a user (e.g., a smoker) desires to receive health benefits from the fullerene molecules. For example, rolling papers that incorporate fullerene molecules according to operations discussed herein may be subject to heating via a flame or other heating element that emits a broad spectrum of visible and/or non-visible frequencies of light. However, and despite what is currently known about interactions between fullerene molecules and light, employing the operations discussed herein to produce a smoke-able product that incorporates fullerene molecules can still allow a user to receive the benefits of the fullerene molecules.

Figure 5:
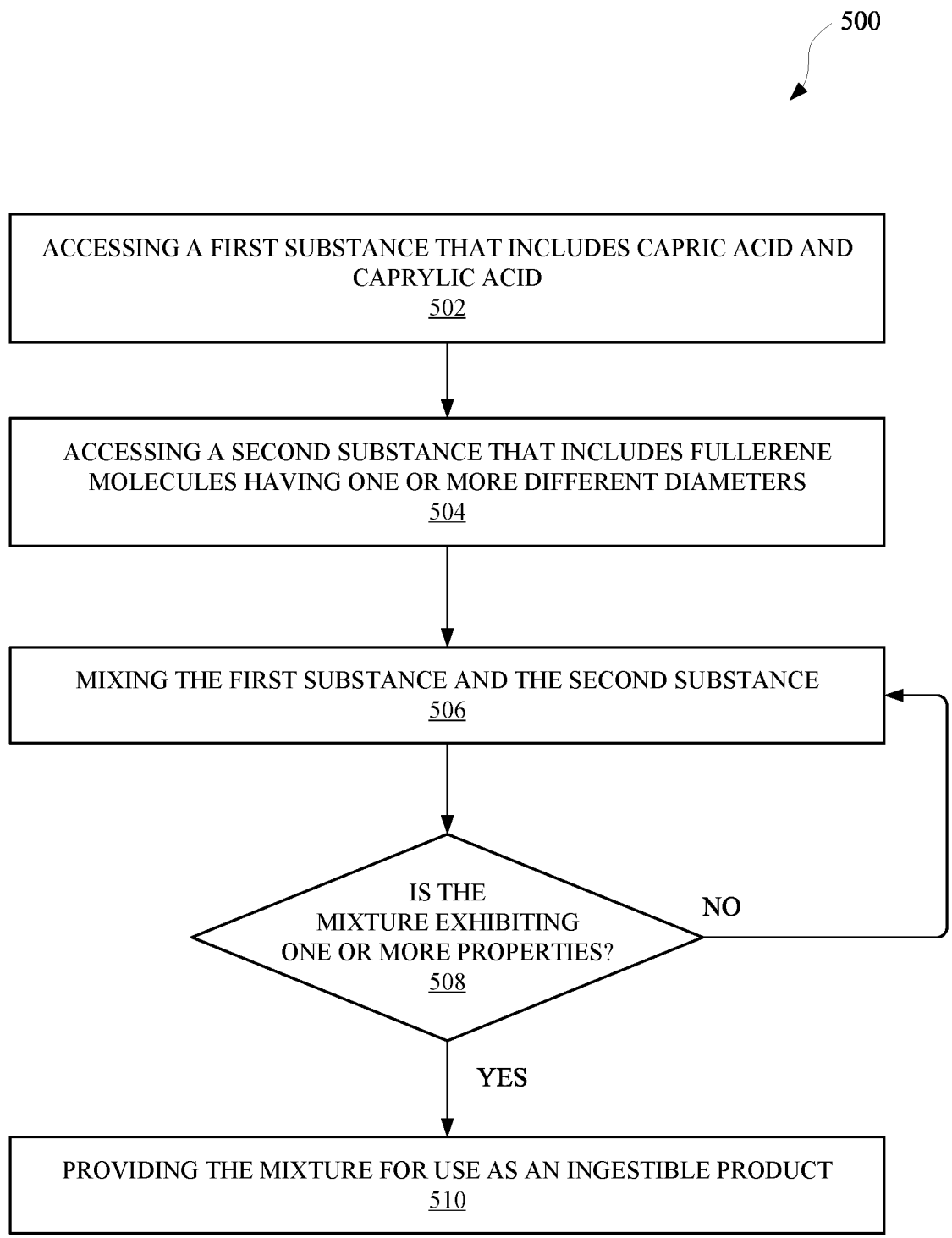
FIG. 5 illustrates a method for producing another ingestible product that includes fullerene molecules.

FIG. 5 illustrates a method 500 for manufacturing an ingestible product that includes fullerene molecules. The method 500 can be performed by employing one or more persons, organisms, chemicals, devices, applications, and/or any suitable combination thereof. The method 500 can include an operation 502 of accessing a first substance that includes capric acid and caprylic acid. In some implementations, the first substance can be a mixture that includes at least 30% capric acid and at least 60% caprylic acid. Alternatively, the first substance can be a mixture that includes at least 30% caprylic acid and at least 60% capric acid. Alternatively, the first substance can be a mixture that includes at least 25% capric acid and at least 55% caprylic acid. Alternatively, the first substance can be a mixture that includes at least 25% caprylic acid and at least 55% capric acid.

The method 500 can proceed from operation 504 to an operation 504, which can include accessing a second substance that includes fullerene molecules, each fullerene molecule having the same or different diameters. Alternatively, or additionally, the second substance can include fullerene molecules, each fullerene molecule having the same or a different number of carbon atoms. In some implementations, the second substance can include some amount of ash, graphite, fullerene, and/or any other combination of carbon atoms. The method 500 can proceed from operation 504 to an operation 506, which can include mixing the first substance and the second substance. In some implementations, the mixing can be performed by an electromechanical device until the mixture exhibits particular properties. For example, the method 500 can include an operation 508 of determining whether the mixture of the first substance and the second substance are exhibiting one or more properties. The one or more properties can include, but are not limited to, reflectance, opacity, viscosity, density, heat of vaporization, color, and/or any other property that can be associated with a mixture. For example, as the first substance and the second substance are being mixed, the opacity and/or color of the mixture can change.

In some implementations, the method 500 can include an optional operation of filtering the mixture until the one or more properties of the mixture further changes. For instance, the mixture can be filtered in order to cause the mixture to be more transparent and/or less opaque. In some implementations, the mixture can be filtered using a filter having pores of 1000 nanometers or greater in order to filter out particles having a length and/or diameter of 1000 nanometers and/or greater. In some implementations, the filter can be a fritted glass filter, and the operation of filtering can be performed multiple times.

When the operation 508 results in the mixture having one or more properties, the method 500 can proceed to an operation 510. Otherwise, the method 500 can return to the operation 506. The operation 510 can include providing the mixture for use as an ingestible product. For example, the ingestible product can be a fluid that can be ingested via the mouth, intravenously inserted, topically applied skin, and/or any other form that a health product can be utilized. In some implementations, the mixture can be incorporated onto a substrate or other material that can be smoked, in order that the fullerene molecules embodied in the mixture can be inhaled. In some implementations, the mixture can be disposed over a wearable latex material, in order that a person wearing the wearable later material will receive the benefits of the fullerene molecules and/or any other substance (e.g., a lubricant) that is disposed over the latex with the mixture. For example, when the mixture is disposed over a latex material, or incorporated into any other substance (e.g., a lubricant), the fullerene can be absorbed into the person or another person (with prior permission from the other person) via a mucous membrane or other membrane for absorbing substances. As a result, the fullerene molecules can inhibit and/or delay a bodily reaction that may otherwise occur during, for example, intercourse or other stimulating activity.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In some implementations, a flexible substrate is set forth as comprising one or more fullerene molecules disposed onto the flexible substrate, wherein a first fullerene molecule of the one or more fullerene molecules has a diameter that is the same or is different from another diameter of a second fullerene molecule of the one or more fullerene molecules, and wherein the one or more fullerene molecules are available for affecting a physiological response of the user or another user when the flexible substrate is employed during intercourse. The flexible substrate can include latex and the fullerene molecules can be incorporated into a lubricant that is disposed over a surface of the flexible substrate. In some implementations, the fullerene molecules can be mixed into the lubricant, and the lubricant can be spread across a surface of a flexible latex substrate. In some implementations, the flexible latex substrate can be a condom, and the lubricant containing the fullerene molecules can be disposed over an outer surface of the condom and/or an inner surface of the condom. In other words, the fullerene molecules can be disposed over an inner surface of the condom in order to inhibit a physiological response of a person wearing the condom, and/or the fullerene molecules can be disposed over an outer surface of the condom in order to inhibit a physiological response of a sexual partner of the person wearing the condom.

In other implementations, a material for receiving a smoke-able product is set forth as including a flexible substrate that can at least partially envelope one or more smoke-able products. The flexible substrate can include one or more fullerene molecules disposed onto the flexible substrate, wherein a first fullerene molecule of the one or more fullerene molecules has a diameter that is the same or is different from another diameter of a second fullerene molecule of the one or more fullerene molecules, and wherein the one or more fullerene molecules are available for inhalation by a user when the flexible substrate is heated to smoke the one or more smoke-able products.

In some implementations, the flexible substrate further comprises: one or more layers of fibrous paper that abut the one or more fullerene molecules. In some implementations, the one or more fullerene molecules at least partially penetrate an outer most surface of the one or more layers of fibrous paper. In some implementations, the flexible substrate further comprises: a carrier solvent that is disposed over a portion of the outer most surface of the layer of fibrous paper. In some implementations, the one or more fullerene molecules are dissolved into the carrier solvent with a concentration that is greater than or equal to 1 gram of fullerene per liter of carrier solvent. In some implementations, the one or more fullerene molecules are dissolved into the carrier solvent with a concentration that is greater than or equal to 2.8 grams of fullerene per liter of carrier solvent.

In some other implementations, a method for manufacturing a product that inhibits coughing is set forth as including operations such as generating a mixture that includes a carbon substance and a liquid. The method can also include an operation of disposing the mixture into a container that comprises one or more surfaces. The method can further include an operation of causing the liquid of the mixture to at least partially evaporate from the container, wherein a portion of the carbon substance remains on the one or more surfaces of the container when the liquid at least partially evaporates from the container. The method can further include an operation of removing the portion of the carbon substance that remains on the one or more surfaces of the container, wherein the portion of the carbon substance includes one or more fullerene molecules. The method can further include an operation of incorporating the portion of the carbon substance with a smoke-able product.

In some implementations, causing the liquid to at least partially evaporate from the container includes: causing an ultrasonic evaporator to evaporate at least some of the liquid from the container. In some implementations, the method can further include an operation of filtering, before generating the mixture, particles of a threshold length from the liquid. In some implementations, the liquid is an oil that contains medium-chain triglycerides (MCT), and oil particles having the threshold length are filtered from the liquid. In some implementations, removing the portion of the carbon substance that remains on the one or more surfaces of the container includes: causing the portion of the carbon substance to be: at least partially displaced from the one or more surfaces and dissolved into an additional liquid, and incorporating the portion of the carbon substance with a smoke-able product includes: disposing the portion of the carbon substance and the additional liquid onto a surface of the smoke-able product.

In some implementations, the portion of the carbon substance includes the one or more fullerene molecules and is dissolved into the additional liquid at a concentration of greater than or equal to 0.1 gram per liter. In some implementations, the portion of the carbon substance includes the one or more fullerene molecules and is dissolved into the additional liquid at a concentration of greater than or equal to 0.25 grams per liter. In some implementations, the method can further include an operation of, subsequent to removing the portion of the carbon substance that remains on the one or more surfaces of the container, and prior to incorporating the portion of the carbon substance with the smoke-able product: filtering the additional liquid to remove carbon molecules that comprise the carbon substance and have a dimension that is greater than or equal to a threshold dimension of 1000 nanometers.

In some implementations, the smoke-able product is a plant and incorporating the portion of the carbon substance with the smoke-able product includes: generating a mixture of the carbon substance and a nitrogen-containing material, wherein the nitrogen-containing material can be absorbed by a growing plant; and providing the mixture of the carbon substance and the nitrogen-containing material to the growing plant or a seed, wherein the providing the mixture to the growing plant or a seed causes one or more fullerene molecules to be relocated to one or more plant portions that are the product of the growing plant or the seed. In some implementations, incorporating the portion of the carbon substance with the smoke-able product includes, when the mixture is provided to the growing plant or seed: causing an electromagnetic field or magnetic field to affect movement of the one or more fullerene molecules through the one or more portions of the plant resulting from the growing plant or the seed.

In yet other implementations, a method for producing a material for relieving disease symptoms is set forth as including operations such as accessing a first substance that includes capric acid and caprylic acid. The method can further include an operation of accessing a second substance that includes fullerene molecules having one or more different diameters. The method can further include an operation of generating a mixture of the first substance and the second sub stance.

In some implementations, generating the mixture includes: causing the mixture to exhibit a first degree of opacity when the first substance and the second substance are mixed, and causing the mixture to be agitated for an amount of time, wherein agitating the mixture causes the mixture to exhibit a second degree of opacity that is less opaque relative to the first degree of opacity. In some implementations, the method can further include an operation of filtering, before generating the mixture, particles of a threshold length from the first substance. In some implementations, generating the mixture includes: causing the mixture to exhibit a first reflectance when the first substance and the second substance are initially mixed, and causing the mixture to be agitated for an amount of time, wherein agitating the mixture causes the mixture to exhibit a second reflectance that is different from the first reflectance.

I claim:

1. A rolling paper for a smoke-able product, the rolling paper comprising:
    a flexible substrate that can at least partially envelope the smoke-able product, the flexible substrate comprising:
        one or more fullerene molecules disposed onto a flexible substrate surface,
            wherein a first fullerene molecule of the one or more fullerene molecules has a diameter that is the same or is different from another diameter, of a second fullerene molecule of the one or more fullerene molecules, that is less than or equal to 1000 nanometers, and
            wherein the one or more fullerene molecules and particles of the smoke-able product are released from the flexible substrate and inhaled by a user upon heating the rolling paper.

2. The rolling paper of claim 1, wherein the flexible substrate further comprises:
    one or more layers of fibrous paper that abut the one or more fullerene molecules.

3. The rolling paper of claim 2, wherein the one or more fullerene molecules at least partially penetrate an outer most surface of the one or more layers of fibrous paper.

4. The rolling paper of claim 3, wherein the flexible substrate further comprises:
    a carrier solvent that is disposed over a portion of the outer most surface of the layer of fibrous paper.

5. The rolling paper of claim 4, wherein the one or more fullerene molecules are present in the carrier solvent with a concentration that is greater than or equal to 1 gram of fullerene per liter of carrier solvent.

6. The rolling paper of claim 4, wherein the one or more fullerene molecules are present in the carrier solvent with a concentration that is greater than or equal to 2.8 grams of fullerene per liter of carrier solvent.

* * * * *